United States Patent
Mitrovic

(10) Patent No.: US 10,543,095 B2
(45) Date of Patent: Jan. 28, 2020

(54) ORTHOPEDIC IMPLANT AND METHOD OF PRODUCING THE IMPLANT

(71) Applicant: Milija Mitrovic, Rostock (DE)

(72) Inventor: Milija Mitrovic, Rostock (DE)

( * ) Notice: Subject to any disclaimer, the term of this patent is extended or adjusted under 35 U.S.C. 154(b) by 0 days.

(21) Appl. No.: 16/066,148

(22) PCT Filed: Dec. 28, 2016

(86) PCT No.: PCT/DE2016/000443
§ 371 (c)(1),
(2) Date: Jun. 26, 2018

(87) PCT Pub. No.: WO2017/114521
PCT Pub. Date: Jul. 6, 2017

(65) Prior Publication Data
US 2019/0015214 A1    Jan. 17, 2019

(30) Foreign Application Priority Data
Dec. 29, 2015   (DE) .......................... 10 2015 016 893

(51) Int. Cl.
*A61F 2/36*   (2006.01)
*B23K 35/26*   (2006.01)
(Continued)

(52) U.S. Cl.
CPC ............ *A61F 2/3609* (2013.01); *B23K 35/24* (2013.01); *B23K 35/26* (2013.01); *B23K 35/327* (2013.01);
(Continued)

(58) Field of Classification Search
CPC .. A61F 2/32; A61F 2/36; A61F 2/3607; A61F 2/3609; A61F 2/3662; A61F 2/367;
(Continued)

(56) References Cited

U.S. PATENT DOCUMENTS

| | | |
|---|---|---|
| 5,037,441 A | 8/1991 | Bouvet |
| 6,214,051 B1 | 4/2001 | Badorf et al. |

(Continued)

FOREIGN PATENT DOCUMENTS

| | | |
|---|---|---|
| DE | 29 21 529 | 12/1980 |
| DE | 690 16 110 | 8/1995 |

(Continued)

OTHER PUBLICATIONS

PCT Examiner Alessandra Mingrino, English translation of the International Search Report of the International Searching Authority for International Application PCT/DE2016/000443, dated Jun. 8, 2017, 2 pages, European Patent Office, HV Rijswijk, Netherlands.
(Continued)

*Primary Examiner* — Marcia L Watkins
(74) *Attorney, Agent, or Firm* — W. F. Fasse

(57) ABSTRACT

An orthopedic implant in the form of a hip joint endoprosthesis includes a ceramic head set onto an anchoring shaft, which is configured and adapted to be inserted and anchored into a bone. The head has an inner blind recess. The anchoring shaft has a tenon. A metallic sleeve having an approximately central through-bore is soldered into the recess of the head. The tenon of the anchoring shaft is inserted and secured in the bore of the sleeve. The head is made of a ceramic based on zirconium dioxide, aluminum oxide or a mixed ceramic, while the sleeve is made of a high strength titanium material. A connection between the head and the sleeve is produced by a silicate ceramic solder that solidifies or hardens in a ceramic firing, and by a subsequently applied glass solder, of which the excess can exit from the recess via the through-bore into a hollow space existing between the sleeve and the tenon.

21 Claims, 3 Drawing Sheets

(51) Int. Cl.
  B23K 35/32    (2006.01)
  B23K 35/24    (2006.01)
  A61F 2/30     (2006.01)
(52) U.S. Cl.
  CPC ............... *A61F 2002/30331* (2013.01); *A61F 2002/30332* (2013.01); *A61F 2002/30354* (2013.01); *A61F 2002/30451* (2013.01); *A61F 2002/30474* (2013.01); *A61F 2002/365* (2013.01); *A61F 2002/3621* (2013.01); *A61F 2310/00017* (2013.01); *A61F 2310/00023* (2013.01); *A61F 2310/00179* (2013.01); *A61F 2310/00209* (2013.01); *A61F 2310/00239* (2013.01)
(58) Field of Classification Search
  CPC .......... A61F 2/3676; A61F 2002/30451; A61F 2002/3613
  See application file for complete search history.

(56) References Cited

U.S. PATENT DOCUMENTS

| | | |
|---|---|---|
| 2006/0188845 A1 | 8/2006 | Serafin, Jr. et al. |
| 2019/0008645 A1 | 1/2019 | Mitrovic |

FOREIGN PATENT DOCUMENTS

| | | |
|---|---|---|
| DE | 197 11 628 | 7/1998 |
| DE | 199 52 918 | 6/2001 |
| DE | 103 40 059 | 2/2005 |
| DE | 603 06 739 | 7/2007 |
| DE | 102011015300 | 9/2012 |
| DE | 102012014345 | 1/2014 |
| EP | 2 742 905 | 6/2014 |
| GB | 2 396 561 | 6/2004 |
| JP | 05-168693 A | 7/1993 |
| WO | WO 2012/010899 | 1/2012 |
| WO | WO 2012/126449 | 9/2012 |

OTHER PUBLICATIONS

English Translation of PCT Written Opinion of the International Searching Authority for International Application PCT/DE2016/000443, dated Jun. 8, 2017, 5 pages, International Bureau of WIPO, Geneva, Switzerland.

Aurica Zothner et al., "Die Evolution des Abutments", Quintessenz der Zahntechnik, Quintessenz Verlags, DE, vol. 35, No. 5, Jan. 1, 2009, pp. 2-16, XP002676248, ISSN: 0340-4641, Retrieved from the Internet: URL:http://www.memodent.nl/upload/content/documents/qz052009_zothner.pdf, especially pp. 10-13, with partial English translation, 3 pages.

Application text and drawings of U.S. Appl. No. 16/066,117, filed Jun. 26, 2018, titled "Orthopedic Implant".

ORTHOPEDIC IMPLANT AND METHOD OF PRODUCING THE IMPLANT

FIELD OF THE INVENTION

The invention relates to an orthopedic implant in the form of a femoral component of a hip joint endoprosthesis with a head of a ceramic material that is set onto an anchoring shaft, which is configured and adapted to be inserted and anchored into a bone.

BACKGROUND INFORMATION

The femoral component of a hip joint endoprosthesis consists essentially of a shaft for anchoring in the core of the long bone or hollow bone of the thigh, and an approximately spherical-segment-like head for replacement of a diseased hip head, which is arranged or mounted on the proximal end of the anchoring shaft in such a manner so that it forms a load carrying unit with the anchoring shaft. While in such prostheses the anchoring shaft and the ball head frequently consist of the same type of material and are inseparably welded together with one another, in a different connection between the prosthesis head and the anchoring shaft a type of plug-connection is provided.

In this, a load-carrying tenon or peg in the form of a cone is arranged on the proximal end of the anchoring shaft, onto which in turn the prosthesis head is plugged or set. Such an arrangement has become known from the DE 2 921 529 A1. In this known arrangement, the connection between the head and the tenon or peg carrying it is releasably embodied, whereby it is possible, during the operation and depending on the indications, to use on the carrying tenon or peg either a head with larger diameter for the replacement of a diseased hip head and thereby to implant a so-called hemi-prosthesis, or instead a head of smaller diameter to supplement or complete this by means of a replacement socket to form a total hip endoprosthesis.

Such hip joint endoprostheses are only reliably utilizable if, in addition to a problem-free anchoring of the prosthesis shaft in the femur, the long time functions of the tenon or peg support that carries the head and of the head itself are also ensured. Thus, especially with conical insertion or plug-in connections typically utilized for prosthesis heads of oxide ceramic for producing a mechanically secure and slip-free clamping or jamming between the cone-shaped, generally metallic, supporting tenon or peg of the anchoring shaft and the metal or ceramic head, there arises the problem of the loosening of the originally mechanically secure connection as well as the disruption or destruction of the surface of the material pairing of head and shaft. Thereby however, corrosion processes can be triggered, which sometimes throw the integrity of the prosthesis completely into question. Moreover, an inadequate fitting of a ceramic head with the metallic tenon or peg can lead to increased stresses in the ceramic, with the result of a subsequent fracture of the implant component. Furthermore, the setting or plugging of a ceramic head onto a shaft left in-situ in the context of a replacement or exchange operation always represents a critical process.

For this reason, an already known measure is to provide a metal sleeve in a ceramic head of a hip joint endoprosthesis, which metal sleeve is joined on the one hand with the ball head and on the other hand with the tenon or peg. In the previously known arrangements, the joining of the sleeve with the ball head occurs either intra-operatively by the operating surgeon or it is already pre-operatively pressed into the ball head. In this regard, an arrangement is known from the U.S. 2006/0188845 A1, in which a metallic sleeve is selectively soldered or shrunken into a similarly metallic blind-hole-type inner recess of a ceramic head.

Moreover, from the DE 10 2012 014 345 A1, a femoral component of a hip joint endoprosthesis of the initially mentioned type has become known, in which the joining of the metallic sleeve with the blind-hole-type inner recess of a ceramic head is achieved pre-operatively in every case, wherein the connection or joint between the ceramic head and the sleeve is produced via a glass solder.

SUMMARY OF THE INVENTION

It is an object of at least one embodiment of the invention to further develop such an implant in such a manner so that the ceramic head and the anchoring shaft are connected or joined with one another pre-operatively in such a manner so that a fixed or secure, non-releasable or non-loosenable connection between the sleeve and the head arises, and so that thereby among other things no abrasive wear particles of the articulating materials of head and shaft can be released.

The above object can be achieved according to at least one embodiment of the invention in that the sleeve is pre-coated with a silicate glass solder that solidifies or hardens in a ceramic firing, that the connection between the ceramic head and the sleeve is produced via a second silicate glass solder, wherein the top covering surface of the sleeve comprises an approximately central through-bore, through which excess liquid second glass solder can escape into a hollow space existing between the sleeve and the seat i.e. the tenon or peg of the shaft.

An especially optimal further preferred embodiment of the implant according to the invention is achieved in that the sleeve and the anchoring shaft consist of the same metallic material, which preferably involves a high strength titanium alloy, generally the alloy Ti-6A1-4V (titanium grade 5).

BRIEF DESCRIPTION OF THE DRAWINGS

In the following the invention will be explained in further detail in connection with an example embodiment illustrated in the drawing. It is shown by.

DETAILED DESCRIPTION OF EXAMPLE EMBODIMENTS OF THE INVENTION

Figure 1:
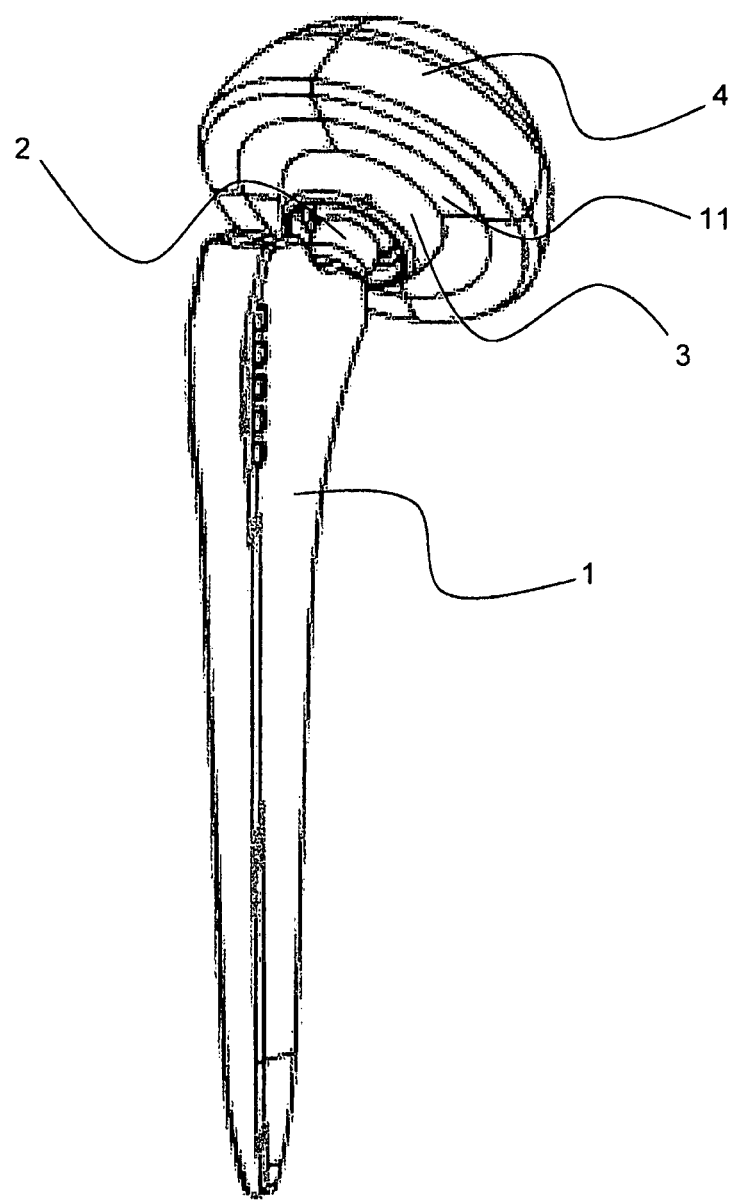
FIG. 1 a hip joint endoprosthesis in a perspective illustration.
Figure 2:
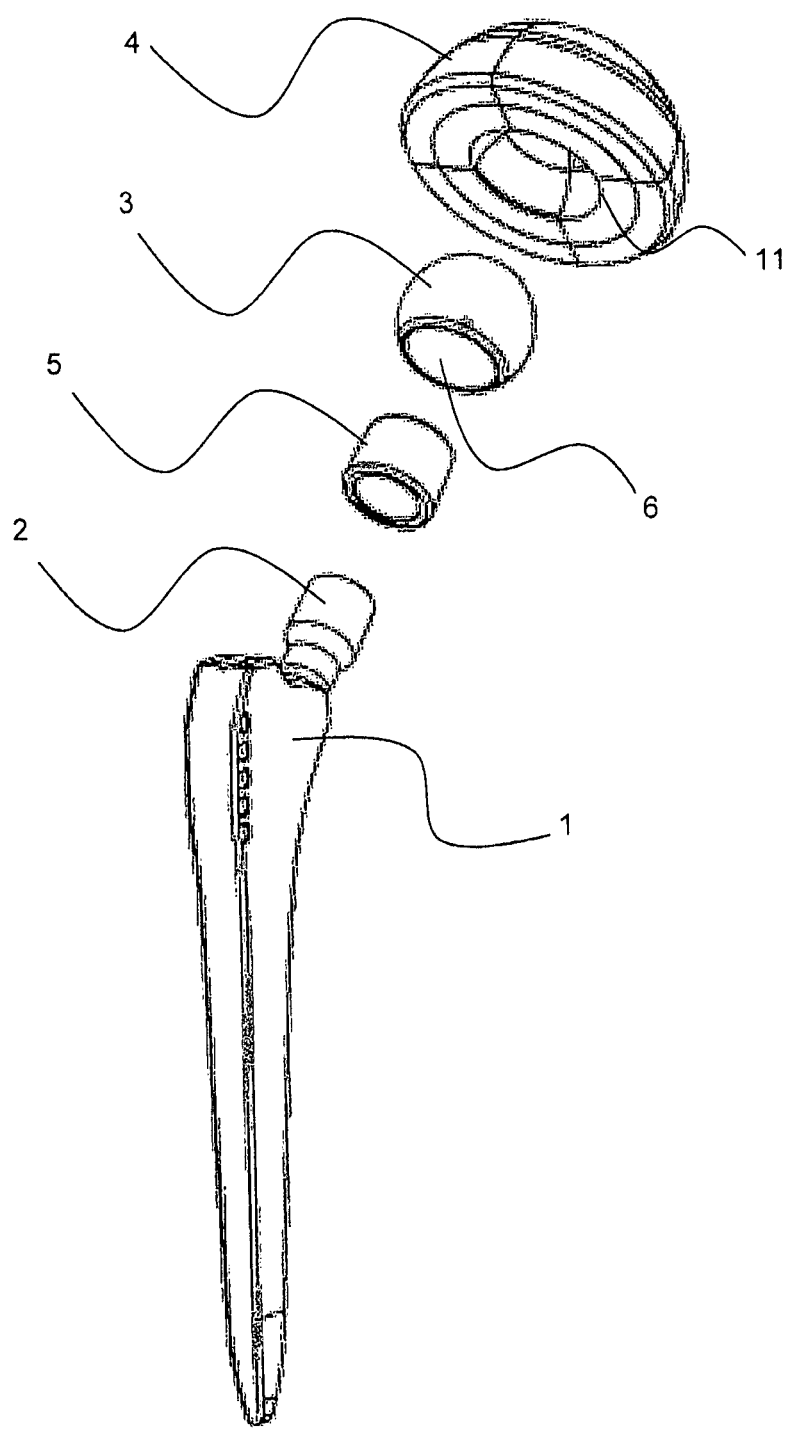
FIG. 2 an exploded illustration of the arrangement according to FIG. 1.
Figure 3:
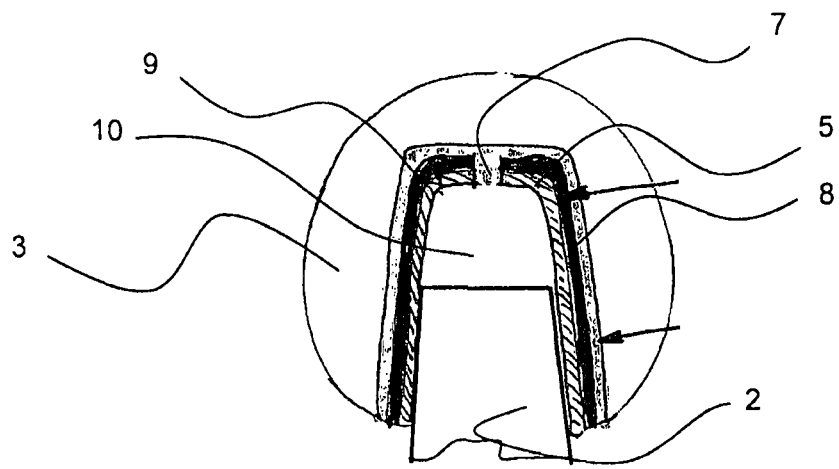
FIG. 3 an enlarged section through the ball head of the hip joint endoprosthesis according to FIG. 1, and FIG. 4 an enlarged section through an alternative ball head of a hip joint endoprosthesis in three different illustrations.

The illustration according to the FIGS. 1 and 2 shows a femoral component of a hip joint endoprosthesis with a shaft 1 for anchoring in the core of the long bone or hollow bone of the thigh of a patient, as well as with a head 3 that can be set or mounted onto a proximal seat 2 of the shaft 1 and that is embodied approximately spherical-segment-like for replacement of the diseased hip head of a patient. This head 3 is inserted into the replacement socket 4 of a total hip endoprosthesis, whereby an additional socket insert 11 in the replacement socket 4, if applicable, achieves a perfect fitting of the two components to one another.

The head 3 consists of an oxide ceramic and comprises a blind-hole-type recess 6, into which a sleeve 5 is soldered, which consists of the same material of which also the shaft 1 as well as the proximal seat 2 (e.g. a tenon or peg 2) of the shaft 1 consist. In the case of the example embodiment described here, this involves the high strength titanium alloy Ti-6A1-4V (titanium grade 5). The top cover surface of the sleeve 5 is provided with a through-bore 7. A silicate glass solder 8 is applied onto the outer surface of the titanium sleeve 5 by an airbrush technique, which among other things effectuates a uniform covering and binding or joining of the titanium oxide before the soldering by means of a firing process. This covering ensures a homogeneous flowing behavior of a subsequently applied silicate glass solder 9. In that regard, the through-bore 7 causes a capillary effect on the liquid glass solder 9. The goal of this action is to prevent the occurrence of oxidic products of the titanium and a droplet formation possibly going along therewith in the area of the sleeve 5, because this could otherwise lead to a fracturing of the sleeve 5.

In the subsequent firing process, the ceramic head 3 is connected or joined by the glass solder 9 with the titanium sleeve 5, wherein this connection or joining is produced via the silicate glass solder 8 that solidifies or hardens in the ceramic firing. While the outer surface of the ceramic head 3 is not modified in this process step, its areas of the inner surface that are treated with the glass solder 9, except for the region of the top covering surface of the titanium sleeve 5 provided with the through-bore 7, are covered by this sleeve 5, so that practically no free or exposed modified surface that interacts with the surroundings exists. While the excess liquid glass solder 9 can escape into the hollow space 10 formed between the sleeve 5 and the seat 2 of the shaft 1, the portion of the glass solder 9 that is solidified or hardened during the firing process by means of soldering forms a securely seated or fixed ceramic layer between the inner surface of the ceramic head 3 and the outer surface of the titanium sleeve 5 and fixedly binds or joins these two components to one another.

Through the titanium sleeve 5 that is soldered-in in this manner, critical stresses in the ceramic head 3, which could otherwise arise during the joining process of the head 3 onto the metallic tenon or peg 2, are reliably avoided. The ceramic ball head 3 articulates with the artificial socket 4 or with the socket insert 11; a contact of the ball head 3 to the surrounding bone does not exist.

Figure 4:
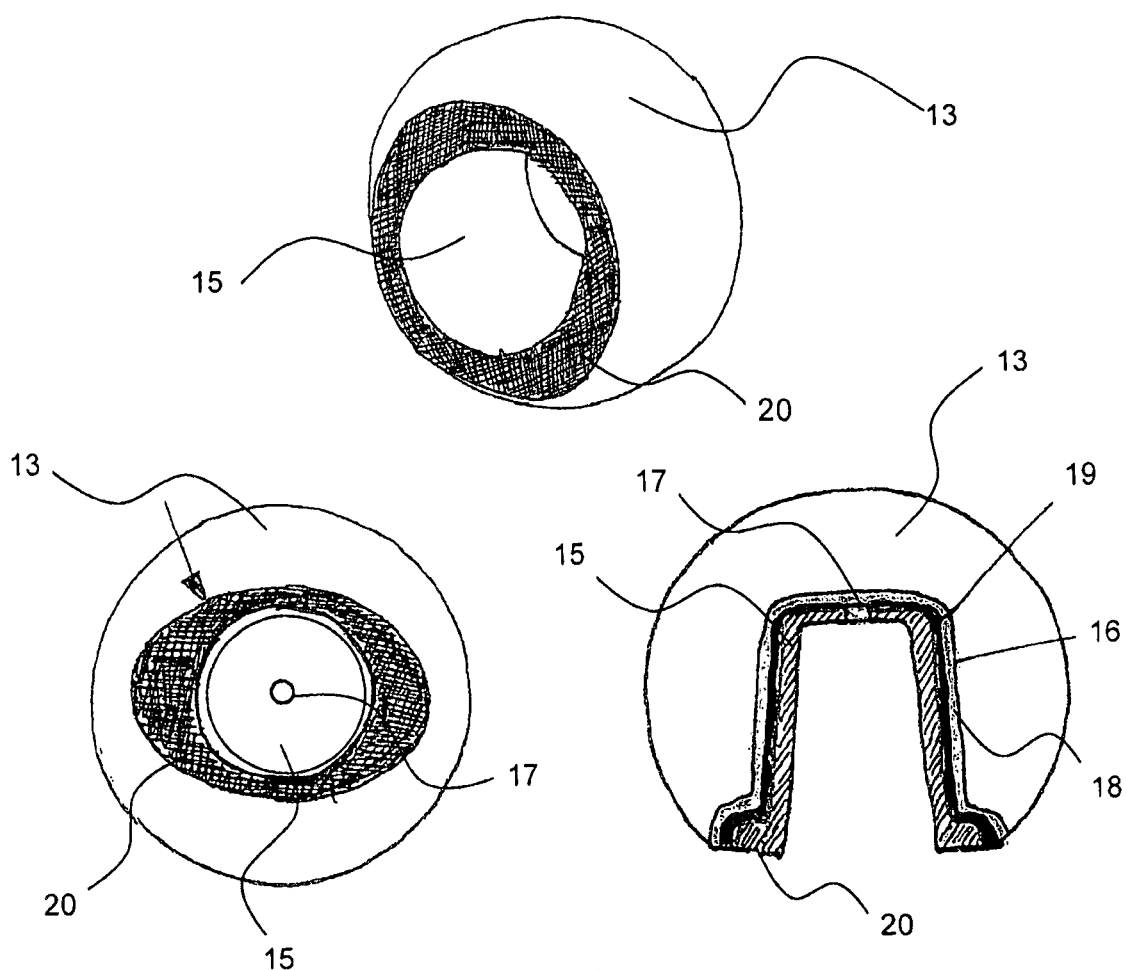

The illustrations of the FIG. 4 in principle show the same ceramic head 13 as it is also shown in the preceding illustrations, and also the sequence of the firing process by means of soldering between the ceramic head 13 and a sleeve 15 of Ti-6A1-4V inserted therein is the same as described above, e.g. with a pre-applied and pre-fired first solder 18. Only in this case the lower widened rim 20 of the sleeve 15 is embodied elliptically. In this form or shape, it serves as an additional protection against improper rotation for the sleeve 15 soldered into the ball head 13, and primarily prevents the influence of torsional forces on the solidified or hardened glass solder 19 between the outer side of the sleeve 15 and the recess 16 of the ball head 13 during rotation motions of the ball head 13, while also in this case excess liquid glass solder 19 can again flow away via a central through-bore 17 into the hollow space formed between the upper part of the sleeve 15 and the upper end region of the seat of the shaft that extends into it.

The invention claimed is:

1. An orthopedic implant configured as a femoral component of a hip joint endoprosthesis, said orthopedic implant comprising:
   - an anchoring shaft that includes a shaft part with a first end configured to be inserted and anchored in a bone, and a tenon at a second end of the shaft part;
   - a head that consists of a ceramic material and has a blind recess therein;
   - a sleeve that includes a metallic sleeve core and a silicate layer that coats a surface of the metallic sleeve core, wherein the sleeve is disposed in the blind recess of the head, the sleeve has therein a hollow interior with an open end, the sleeve has a through-bore communicating into the hollow interior at a second end of the sleeve opposite the open end, and the hollow interior is configured and adapted to receive the tenon of the anchoring shaft inserted therein with a hollow space remaining in the hollow interior between the tenon and the second end of the sleeve; and
   - a joining layer that is formed of a silicate glass solder and that joins together the head and the sleeve disposed in the blind recess of the head.

2. The orthopedic implant according to claim 1, wherein the silicate layer of the sleeve is a layer as results from hardening an applied silicate solder by a ceramic firing process, wherein the applied silicate solder is a silicate glass solder or a silicate ceramic solder.

3. The orthopedic implant according to claim 1, wherein the silicate layer is a silicate ceramic layer.

4. The orthopedic implant according to claim 1, wherein the surface of the metallic sleeve core coated by the silicate layer is an outer surface of the metallic sleeve core.

5. The orthopedic implant according to claim 1, wherein a portion of the silicate glass solder of the joining layer extends through the through-bore and into the hollow space in the hollow interior of the sleeve.

6. The orthopedic implant according to claim 1, wherein the blind recess of the head is cylindrical, and an outer surface of the sleeve is cylindrical.

7. The orthopedic implant according to claim 1, wherein an inner surface of the head bounding the blind recess has a tapered conical frustum shape, and an outer surface of the sleeve has a tapered conical frustum shape.

8. The orthopedic implant according to claim 1, wherein the blind recess includes an inward tapered conical frustum shaped portion and outward enlarged elliptical portion, and wherein an outer surface of the sleeve includes a tapered conical frustum shaped portion and an enlarged rim having an elliptical shape that fits into the outward enlarged elliptical portion of the blind recess.

9. The orthopedic implant according to claim 1, wherein the blind recess of the head and the sleeve are each respectively configured and dimensioned so that the sleeve fits into the recess with a space therebetween, and the joining layer fills the space.

10. The orthopedic implant according to claim 1, wherein the tenon of the anchoring shaft and the metallic sleeve core both consist of a same metallic material.

11. The orthopedic implant according to claim 10, wherein the metallic material is a titanium alloy.

12. The orthopedic implant according to claim 1, wherein the ceramic material of the head is an oxide ceramic.

13. The orthopedic implant according to claim 1, wherein the through-bore is configured so that a portion of the silicate glass solder escapes from the blind recess of the head, through the through-bore, into the hollow space in the hollow interior of the sleeve when the sleeve is being disposed into the blind recess of the head.

14. An orthopedic implant configured as a femoral component of a hip joint endoprosthesis comprising an anchoring shaft, and a head consisting of a ceramic material, which is set onto the anchoring shaft, which is configured to be inserted into a bone and anchorable therein, wherein the ceramic head comprises a cylinder-shaped blind-hole-type inner recess and the anchoring shaft has a tenon that is inserted into this recess, wherein a similarly cylinder-shaped metallic sleeve is soldered into the recess of the head, via which sleeve the ceramic head is connected with the tenon, wherein the sleeve is pre-coated by a first silicate glass solder that solidifies or hardens in a ceramic firing, wherein the connection between the ceramic head and the sleeve is produced via a second silicate glass solder, and wherein a covering surface of the sleeve comprises a central through-bore through which excess liquid second glass solder can escape into a hollow space existing between the sleeve and the tenon of the anchoring shaft.

15. The orthopedic implant according to claim 14, characterized in that the ceramic material of the head is based on zirconium dioxide.

16. The orthopedic implant according to claim 14, characterized in that the ceramic material of the head is based on aluminum oxide.

17. The orthopedic implant according to claim 14, characterized in that the ceramic material of the head is a mixed ceramic.

18. The orthopedic implant according to claim 14, characterized in that the anchoring shaft including the tenon, and the sleeve consist of a same metallic material.

19. The orthopedic implant according to claim 14, characterized in that the anchoring shaft including the tenon, and the sleeve consist of a high strength titanium alloy Ti-6A1-4V.

20. A method of making the orthopedic implant according to claim 1, comprising the steps:
   a) applying a silicate solder onto the surface of the metallic sleeve core;
   b) after the step a), performing a ceramic firing process to harden the silicate solder and form thereof the silicate layer on the surface of the metallic sleeve core;
   c) after the step b), applying the silicate glass solder onto at least one of the sleeve and the blind recess of the head;
   d) after the step c), inserting the sleeve into the blind recess of the head; and
   e) after the steps c) and d), firing the silicate glass solder so as to form thereof the joining layer that joins together the head and the sleeve disposed in the blind recess of the head.

21. The method according to claim 20, wherein, during the step d), a portion of the silicate glass solder escapes from the blind recess of the head, through the through-bore, into the hollow space in the hollow interior of the sleeve.

* * * * *

UNITED STATES PATENT AND TRADEMARK OFFICE
CERTIFICATE OF CORRECTION

PATENT NO. : 10,543,095 B2
APPLICATION NO. : 16/066148
DATED : January 28, 2020
INVENTOR(S) : Milija Mitrovic Page 1 of 1

It is certified that error appears in the above-identified patent and that said Letters Patent is hereby corrected as shown below:

On the Title Page

<u>Item (56), Page 2 OTHER PUBLICATIONS,</u>
Line 9, replace "qz052009_zothner.pdf" with --qz_05_2009_zothner.pdf--;

In the Specification

<u>Column 2,</u>
Line 39, replace "Ti-6A1-4V" with --Ti-6AI-4V--;

<u>Column 3,</u>
Lines 9 and 54, replace "Ti-6A1-4V" with --Ti-6AI-4V--;

In the Claims

<u>Column 6,</u>
Lines 6/7, replace "Ti-6A1-4V" with --Ti-6AI-4V--.

Signed and Sealed this
Fifteenth Day of September, 2020

Andrei Iancu
*Director of the United States Patent and Trademark Office*